United States Patent [19]

Roberts

[11] Patent Number: 4,771,783

[45] Date of Patent: * Sep. 20, 1988

[54] FLAT, CONFORMABLE, BIOMEDICAL ELECTRODE

[75] Inventor: Charles W. Roberts, Hudson, Wis.

[73] Assignee: Minnesota Mining and Manufacturing Company, St. Paul, Minn.

[*] Notice: The portion of the term of this patent subsequent to Mar. 2, 2005 has been disclaimed.

[21] Appl. No.: 915,138

[22] Filed: Oct. 3, 1986

[51] Int. Cl.$^4$ .......................... A61B 5/04; A61N 1/04
[52] U.S. Cl. .................... 128/640; 128/798; 128/802
[58] Field of Search ............... 128/639–641, 128/798, 802, 803,

[56] References Cited

U.S. PATENT DOCUMENTS

| 3,170,459 | 2/1965 | Phipps et al. | 128/640 |
| 3,865,770 | 2/1975 | Blake | 260/27 R |
| 4,008,721 | 2/1977 | Burton | 128/802 |
| 4,067,342 | 1/1978 | Burton | 128/798 |
| 4,409,981 | 10/1983 | Lundberg | 128/640 |
| 4,413,080 | 11/1983 | Blake | 524/187 |
| 4,422,461 | 12/1983 | Glumac | 128/798 |
| 4,458,696 | 7/1984 | Larimore | 128/798 |
| 4,522,211 | 6/1985 | Bare et al. | 128/640 |
| 4,524,087 | 6/1985 | Engel | 128/639 X |
| 4,524,775 | 6/1985 | Rasmussen | 128/640 |
| 4,539,996 | 9/1985 | Engel | 128/640 |
| 4,543,958 | 10/1985 | Cartmell | 128/640 |
| 4,554,924 | 11/1985 | Engel | 128/640 |
| 4,569,960 | 2/1986 | Blake | 524/145 |
| 4,657,023 | 4/1987 | Kuhn | 128/640 |
| 4,679,563 | 7/1987 | Wada et al. | 128/640 |

FOREIGN PATENT DOCUMENTS 0097436 1/1984 European Pat. Off. .
1470698 1/1967 France .

Primary Examiner—Lee S. Cohen
Attorney, Agent, or Firm—Donald M. Sell; William D. Bauer

[57] ABSTRACT

A biomedical electrode (10) adapted to be applied to a body and adapted to be electrically and mechanically connected to an electrical lead wire (14). The electrode (10) contains a protective, electrically insulative web 12) and an adhesive (16) adjacent one side of the web (12) which is adapted to be oriented to the body. A release liner (18) is placed between the web (12) next to adhesive (16) to facilitate removal and placement of an electrical lead wire (14). An electrically conductive film (22) is positioned adjacent the adhesive (16) opposite the release liner (18). Finally, another layer of adhesive (24) which is electrically conductive is positioned adjacent the electrically conductive film (22) opposite the layer (16of adhesive, which electrically conductive adhesive (24) is adapted to be applied to a body. Alternatively, the electrode (10) has a metallic coating (34) applied to the bottom side of a protective, electrically insulative web (32). A release line (18) separates the metallic coating (34) of the protective web (32) from an electrically conductive adhesive (24) which is adapted to be applied to a body.

6 Claims, 3 Drawing Sheets

FLAT, CONFORMABLE, BIOMEDICAL ELECTRODE

RELATED APPLICATION

This application is a continuation-in-part of application Ser. No. 06/892,691, filed Aug. 1, 1986, now U.S. Pat. No. 4,727,880.

BACKGROUND OF THE INVENTION

The present invention relates generally to biomedical electrodes.

Biomedical electrodes are useful for both stimulation and body monitoring functions. Stimulation uses of biomedical electrodes include transcutaneous electronic nerve stimulation (TENS) for the treatment of pain and neuromuscular stimulation (NMS) as, for example, treatment for scoliosis. Body monitoring uses for biomedical electrodes include electrocardiogram (ECG) for monitoring hear activity.

Among biomedical electrodes in existence are those of Phipps et al., Cartmell and Larimore. Phipps et al in U.S. Pat. No. 3,170,459 discloses a biomedical instrumentation electrode constructed from multiple plies of discs made from a relatively inflexible material, i.e., cork. The electrode utilizes a conductive gel to establish electrical contact with the body. Cartmell in U.S. Pat. No. 4,543,958 discloses a medical electrode assembly. The electrode has a flexible, dimensionally stable substrate which is striped with an electrically conductive paint. The electrode is then clamped into a bulky cable connector. Larimore in U.S. Pat. No. 4,458,696 (assigned to Minnesota Mining and Manufacturing Company) discloses a TENS electrode with a raised structure to permit entry of and attachment to a tubular electrical conductor.

These electrodes suffer from several deficiencies including that all are "high profile" electrodes and that the electrodes do not "conform" well to the body.

SUMMARY OF THE INVENTION

The present invention provides a biomedical electrode which is (1) flatter and more conformable, (2) has a very low profile, (3) may be trimmed to differing shapes, (4) has flexibility in lead wire insertion direction, and (5) allows the reuse of the lead wire. The electrode of the present invention is flatter and more conformable to body contours and body movement than prior electrodes. The electrode relies on an adhesive contact with a flat electrical conductor as opposed to rubber connector strips or snaps. the electrode has a very low profile which makes it suitable to be worn under tight clothing and to be comfortable when slept upon or when leaned against, as for example, when sitting in a chair. The electrode may be trimmed to virtually any size or shape to allow adaptability in placement and location. The electrode allows for flexibility in lead wire insertion and allows for the lead wire to be inserted from the end of the electrode or from either side. The reuseability of the lead wire leads to economy for use of the biomedical electrode.

The present invention provides a biomedical electrode adapted to be applied to a body and adapted to be electrically and mechanically connected to an electrical lead wire. The electrode has a protective, electrically insulated web. The electrode also has a first layer of adhesive adjacent one side of the protective, electrically insulative web, that side being adapted to be oriented toward the body. The electrode has a release liner adjacent the first layer of adhesive opposite said protective, electrically web. The release liner has a release agent facing the first layer of adhesive the release liner covering only a portion of the surface area of the protective, electrically insulative web. The electrode contains an electrically conductive film positioned adjacent the first layer of adhesive opposite said release liner. The electrode further contains an electrically conductive film positioned adjacent the first layer of adhesive opposite said release liner. The electrode further contains a second layer of adhesive which is electrically conductive and positioned adjacent the electrically conductive film opposite the first layer of conductive adhesive and adapted to be applied to the body. In a preferred embodiment, the electrically conductive film is a metallic coating on a self supporting conductive film.

BRIEF DESCRIPTION OF THE DRAWING

The foregoing advantages, construction and operation of the present invention will become more readily apparent from the following description and accompanying drawings in which.

DETAILED DESCRIPTION OF THE PREFERRED EMBODIMENTS

Figure 1:
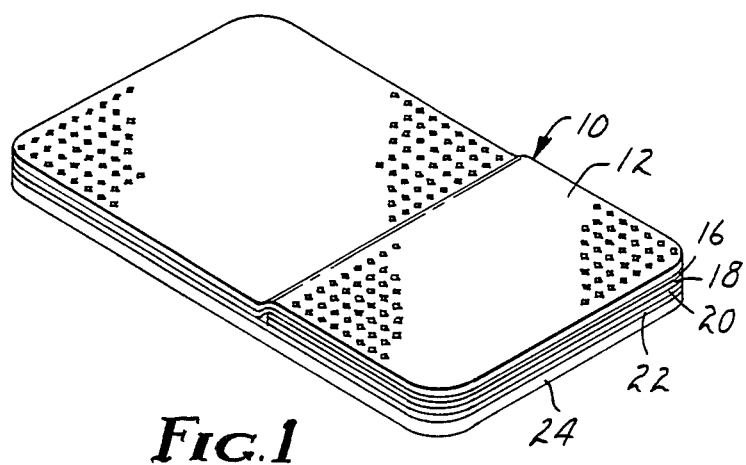
FIG. 1 is isometric view the biomedical electrode of the present invention.

FIG. 1 illustrates an isometric view of a preferred embodiment view of the biomedical electrode 10 of the present invention. The biomedical electrode 10 is also shown in expanded side view of FIG. 2. The top of the biomedical electrode 10 is a protective, electrically insulative web 12. Web 12 protects the top of biomedical electrode 10 from physical damage and covers lead wire 14 when it is inserted in the biomedical electrode 10 to help secure lead wire 14 in place. Web 12 is electrically insulative to confine the electrical signals used in the biomedical electrode to the lead wire 14 or to the body (not shown). As shown in FIG. 1, web 12 is preferably perforated making web 12 more conformable to the body contour and for esthetics. The perforations also assist in the tearability of web 12 once it is desired to remove lead wire 14 from the biomedical electrode 10. In a preferred embodiment, web 12 is approximately 4 mils (1.0 millimeters) thick and is constructed from a pigmented low molecular weight polyethylene film.

Web 12 is attached to the remainder of biomedical electrode 10 with a pressure sensitive adhesive 16. In a preferred embodiment, the pressure sensitive adhesive 16 is an acrylate adhesive. A release liner 18, which is removable, is placed beneath pressure sensitive adhesive 16 covering a portion of the surface area of biomedical electrode 10. Release liner 18 facilitates the lifting of web 12 away from the remainder of the biomedical electrode 10 in order that lead wire 14 may be inserted and web 12 subsequently reapplied securing lead wire 14 in biomedical electrode 10. In a preferred embodiment, release liner 18 is a Polyslick TM material as manufactured by James River Corporation, H. P. Smith Division, Bedford Park, Ill. A conductive adhesive 20 is positioned in the biomedical electrode 10 below release liner 18. Conductive adhesive 20 need only cover a portion of the surface area of biomedical electrode 10 to which lead wire 14 may be positioned. In a preferred embodiment, conductive adhesive 20 covers approximately the same surface area of biomedical electrode 10 as does release liner 18. This allows for relative general ease in the positioning of lead wire 14 once release liner 18 has been removed. In a preferred embodiment, conductive adhesive 20 is made conductive through the inclusion of silver particles. In a preferred embodiment, a resistivity measurement using a one inch square brass plate above and below the adhesive measures approximately 0.01 ohms. The exact conductivity of conductive adhesive 20, of course, depends upon the end use to which biomedical electrode 10 is intended. Generally, it is expected that resistivities of conductive adhesive may generally range up to one ohm. In another embodiment, approximately ten ohms may be sufficient and higher resistivities may be allowable in other embodiments and for other uses for biomedical electrode 10. Conductive adhesive, especially conductive adhesives containing silver particles are widely available. An example of a suitable adhesive is a solvent based acrylate adhesive containing silver particles about 3 mils (0.76 mm) in diameter which is coated through a knife coater at about 12 mils (3.05 mm) thickness. The coated adhesive is heated to drive off the solvent resulting in an adhesive layer of about 1.0 mils (0.38 mm) in thickness. Note that the silver particles are larger than the thickness of the resulting adhesive giving the layer is needed electrical conductivity. An adhesive similar to this but which has been coated on aluminum is available as X1170 foil tape from Minnesota Mining and Manufacturing Company, St. Paul, Minn. Below conductive adhesive 20 an electrically conductive film 22, preferably a metal vapor coated conductive film, covers a large portion of the surface area of biomedical electrode and, in a preferred embodiment, covers the entire surface of biomedical electrode 10. The purpose of electrically conductive film 22 is to disburse the current delivered by or received by biomedical electrode 10 over a larger portion of the surface area of biomedical electrode 10. Electrically conductive film 22 may also operate to provide an ion barrier between the insertable lead wire 14 and the body. In a preferred embodiment, the electrically conductive film is an ethylene vinyl acetate loaded with approximately 28% carbon or a, Velostat ® film manufactured by Minnesota Mining and Manufacturing Company, Saint Paul, Minn. in either case coated top side with a $7 \times 10^{-8}$ to $1.2 \times 10^{-7}$ meters thick vapor coat of aluminum or silver. In a preferred embodiment, electrically conductive film 22 is approximately 3 mils (0.76 millimeters) thick. As indicated, conductive adhesive 24 operates to secure biomedical electrode 10 to the body to biomedical electrode 10 or visa versa. It is preferred that conductive adhesive 24 have better cohesion than adhesion in order to facilitate the ease in which the biomedical electrode 10 may be removed from the body. Conductive adhesive 24 may generally have a volume resistivity of the range from 50 to 200 ohm-centimeters although lower and high volume resistivities may work for some uses of the biomedical electrode 10. In a preferred embodiment, conductive adhesive 24 is from 10 mils (2.5 millimeters) to 60 mils (15.2 millimeters) thick. In a reuseable electrode it is preferred that the conductive adhesive 24 be from 30 mils (7.6 mm) to 44 mils (11.2 mm) thick. In a disposable electrode it is preferred that the conductive adhesive be from 10 mils (2.5 mm) to 24 mils (6.3 mm) thick. An example of a conductive adhesive 24 desirable for a reuseable electrode is described in U.S. Pat. No. 3,865,770, Blake, Water-Dispersable Pressure-Sensitive Adhesive, Tape Made Therewith, and Novel Tackifiers Therefor, which is hereby incorporated by reference. It is preferred that the adhesive in Blake be modified and the following ingredients used:

| Ingredient | Dry Weight Grams | Dry Weight Percent |
| --- | --- | --- |
| Copolymer: Butyl Acrylate & Acrylic Acid in 3:1 ratio | 83.177 | 40.945 |
| Glycerin | 20 | 9.8452 |
| Butanediol | 20 | 9.8452 |
| Sorbitol | 20 | 9.8452 |
| Methyl diethanolamine (MDEA) | 28 | 13.783 |
| Potassium Chloride (KCl) | 6.9678 | 3.4300 |
| Foral AX (hydrogenated wood rosin) | 25 | 12.306 |
| Total | 203.14 | 100.04 |

An example of a conductive adhesive 24 desirable for a disposable electrode is described in U.S. Pat. No. 4,554,924, Engel, Conductive Adhesive and Biomedical Electrode, which is hereby incorporated by reference. It is preferred that the adhesive in Engel be modified and the following ingredients be used:

| Ingredient | Dry Weight Grams | Dry Weight Percent |
| --- | --- | --- |
| 1,4 Butanediol | 45 | 6.3993 |
| Glycerin | 75 | 10.665 |
| Sorbitol | 290 | 41.240 |
| K739, Polyacrylic | 17 | 2.4175 |
| Potassium Hydroxide | 3.25 | 0.46217 |
| Total Water | 155 | 22.042 |
| Acrylic Acid | 115 | 16.354 |
| Irgacure | 0.51635 | 0.07343 |
| Tegbm | 2.3186 | 0.32972 |
| Methyl ethyl hydroquinone | 0.12 | 0.01706 |
| Total | 703.20 | 100.04 |

Optionally, a second release liner (not shown) may be provided below conductive adhesive 24 to facilitate transportation and storage of biomedical electrode 10 before use or between uses.

Biomedical electrode 10 may be utilized by applying the biomedical electrode 10 to a body being secured by conductive adhesive 24. The protective, electrically insulative web 12 may be lifted since release liner 18 prevents the protective, electrically insulative web 12 from sticking to conductive adhesive 20. Once the protective insulative web 12 is lifted, release liner 18 may be removed and discarded. At this time, lead wire 14 may be inserted so that noninsulated portion 26 of lead wire 14 is positioned over conductive adhesive 20. Lead wire 14 also has an insulative portion 28 which extends from beneath the confines of protective, electrically insulative web 12 and may be connected to suitable electronic equipment intended to utilize biomedical electrode 10. Lead wire 14 may be a copper wire whose insulated portion 28 is insulated with any suitable insulation, as for example, rubber or plastic. The end of noninsulated portion 26 of lead wire 14 is a flat crimped on conductor plate 30. Conductor plate 30 is flat which facilitates the biomedical electrode 10 being of low profile, flat and conformable to the body. Conductor plate 30 may, for example, be a zinc plated copper or, optionally, a silver plated copper with a chloride treatment.

Figure 2:
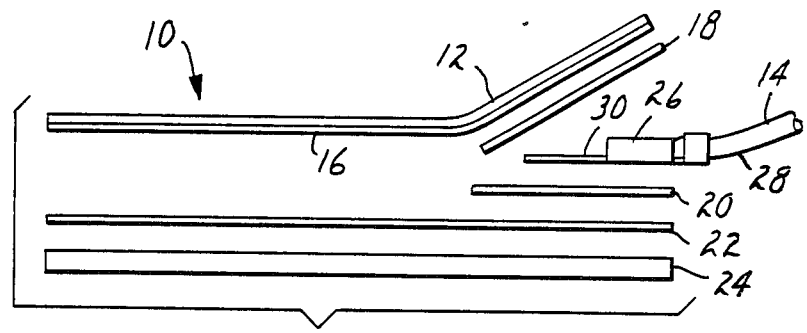
FIG. 2 is a side view of an embodiment of the biomedical electrode of the present invention with a double coated release liner and electrical lead wire illustrated.
Figure 3:
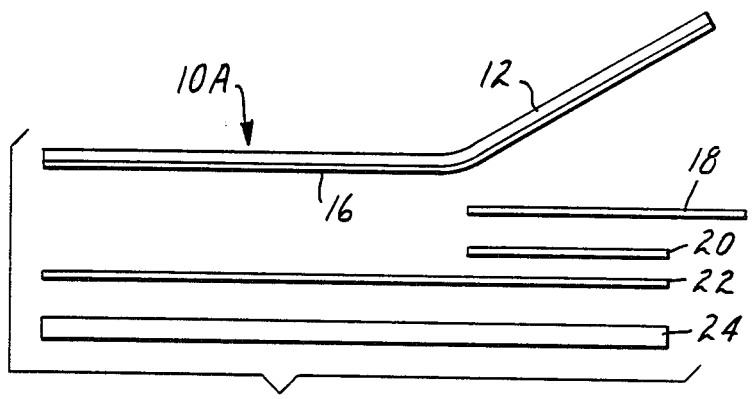
FIG. 3 is a side view of an embodiment of the biomedical electrode of the present invention with an extended release liner.

FIG. 3 illustrates an alternative embodiment for the biomedical electrode 10A of the present invention. The construction of the biomedical electrode 10A in FIG. 3 is similar to the biomedical electrode 10 in FIG. 2 except that protective, electrically insulative web 12, pressure sensitive adhesive 16 and release liner 18 extend from one edge of conductive adhesive 20, electrically conductive film 22 and conductive adhesive 24. Having these items extend beyond the edge facilitates the lifting of protective, electrically insulative web 12 in order that release liner 18 may be removed and lead wire 14 inserted.

Figure 4:
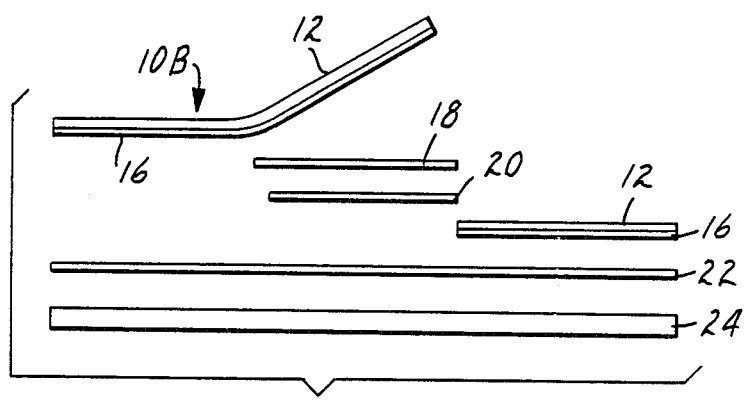
FIG. 4 is a side view of an embodiment of the biomedical electrode of the present invention with a center located release liner.

FIG. 4 illustrates another expanded side view of another embodiment of the biomedical electrode 10B of the present invention. The embodiment illustrated in FIG. 4 is similar with that as biomedical electrode 10 illustrated in FIG. 2 with the exception that the portion of the surface area of biomedical electrode 10 which is covered by release liner 18 and conductive adhesive 20 is positioned centrally in the biomedical electrode 10. This embodiment illustrates that protective insulative web 12, as well as pressure sensitive adhesive 16 may be separated into two portions. Biomedical electrode 10B as illustrated in FIG. 4 operates as before, protective insulative web 12 is lifted, release liner 18 is removed and lead wire 14 is inserted over conductive adhesive 20.

In the embodiments of biomedical electrode illustrated in FIGS. 1-4, a single sheet release liner 18 is illustrated. In these embodiments, release liner 18 is coated both sides with a release agent allowing the release liner 18 to release both from pressure sensitive adhesive 16 and conductive adhesive 20.

Figure 5:
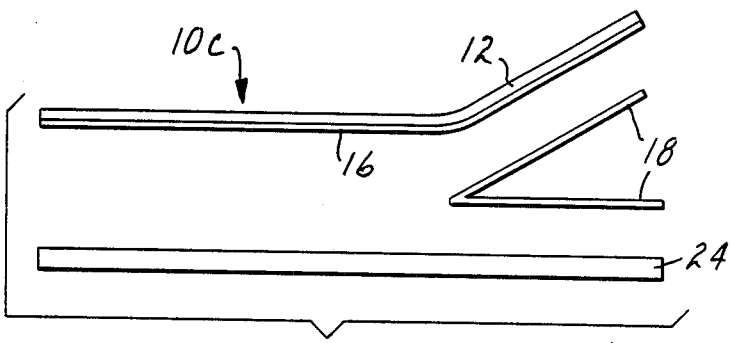
FIG. 5 is a side view of an embodiment of the biomedical electrode of the present invention with a single sided folded release liner.

Another embodiment of biomedical electrode 10C is illustrated in a side exploded view in FIG. 5. The biomedical electrode 10C illustrated in FIG. 5 also contains a protective electrically insulative web 12 and a pressure sensitive adhesive 16. The biomedical electrode 10 also contains a release liner 18. Release liner 18 is illustrated as being folded with the closed side fold being positioned interiorly with respect to biomedical electrode 10 and the open side fold being positioned near an edge of the protective, electrically insulative web 12. The release liner 18 as illustrated in FIG. 5 may be coated on only one side, the outside of release liner 18 as it is folded so that the release agent still contacts pressure sensitive adhesive 16 and conductive adhesive 24. As in the other embodiments, the biomedical electrode 10 C illustrated in FIG. 5 contains conductive adhesive 24 preferably along the entire bottom surface area of biomedical electrode 10. Conductive adhesive 24 is the same as and performs the same purpose as conductive adhesive 24 in FIGS. 1-4. Note that the biomedical electrode 10C illustrated in FIG. 5 is missing electrically conductive adhesive 20 and electrically conductive film 22. As noted earlier, electrically conductive film 22 was used to facilitate the dispersion of electrical currents over the entire surface of biomedical electrode. In situations where such dispersion is not required or such dispersion is not required to be achieved as well as can be achieved with the electrically conductive film 22, the electrically conductive film 22 may be omitted. With the omission of electrically conductive film 22, electrically conductive adhesive 20 is also no longer needed. Electrically conductive adhesive 20 was utilized to secure lead wire 14 when it was positioned within biomedical electrode 10. With the embodiment of the biomedical electrode 10C illustrated in FIG. 5 when release liner 18 is removed, lead wire 14 may be inserted in its place and is secured between protective insulative web 12 by pressure sensitive adhesive 15 and conductive adhesive 24.

Figure 6:
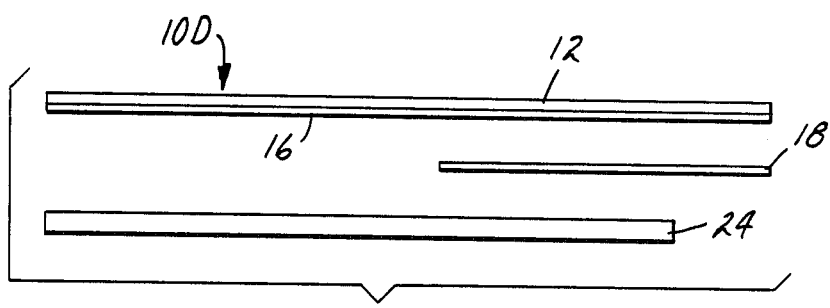
FIG. 6 is a side view of an embodiment of the biomedical electrode of the present invention with an extended release liner and protective web.

The biomedical electrode 10D as illustrated in FIG. 6 is constructed similarly to the embodiment of biomedical electrode 10C illustrated in FIG. 5 with the exception being that protective insulative web 12, pressure sensitive adhesive 15 and release liner 18 extend beyond an edge of conductive adhesive 24 (as in FIG. 3) to facilitate lifting of protective insulative web 12 and removal of release liner 18.

Figure 7:
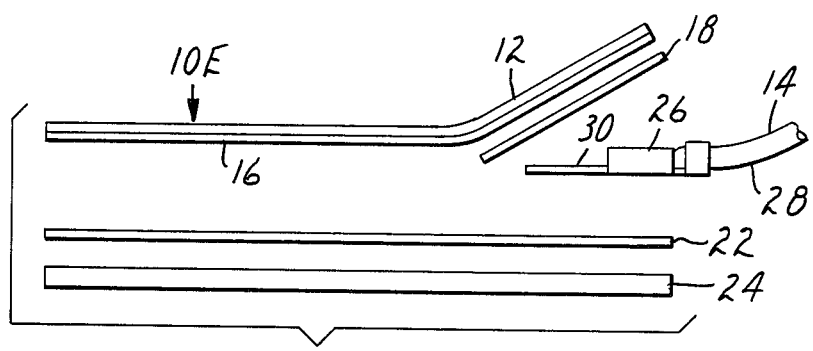
FIG. 7 is a side view of an embodiment of the biomedical electrode of the present invention.

The biomedical electrode 10E illustrated in FIG. 7 is similar to the biomedical electrode 10 illustrated in FIG. 2. Biomedical electrode 10E omits electrically conductive adhesive 20 (shown in FIG. 2) and since electrically conductive adhesive 20 has been omitted release liner 18 need only be release coated on the side facing adhesive 16. As in FIG. 2, the biomedical electrode 10E of FIG. 6 has a protective, electrically insulative web 12 which is secured to the remainder of the biomedical electrode 10E with a layer of adhesive 16. It is preferred that layer of adhesive 16 be a pressure sensitive adhesive. As stated above, release liner 18 covers a portion of the surface area of layer of adhesive 16 and is release coated at least on its top side facing layer of adhesive 16. An electrically conductive film 22 is positioned below both adhesive 16 and release liner 18. It is preferred that electrically conductive film be a metallic coated electrically conductive substrate such as an aluminum vapor coat of from 200 to 1200 angstroms thick on a 28% carbon loaded ethylene vinyl acetate substrate. The metallic vapor coat shoul be the top side of the electrically conductive film 22 facing said release liner 18. Generally, the electrical resistance over the length of the electrically conductive film should be less than or equal to 1 ohms per inch (0.39 ohms per centimeter) of electrically conductive film 22. An electrically conductive adhesive 24 of the same as described with respect to FIG. 2, is than located below electrically conductive film 22 opposite the release liner 18 or layer of adhesive 16. Optionally, a second release liner (not shown) may be then applied to electrically conductive adhesive 24. The electrode is utilized by after first removing the release liner from electrically conductive adhesive 24 if any, applying the biomedical electrode to the body with electrically conductive adhesive 24. Protective web 12 may then be lifted and release liner 18 removed. Lead wire 14 is then inserted into the located where release liner 18 was removed and protective web 12 is secured over lead wire 14. The conductor plate 30 part of the noninsulated portion 26 of lead wire 14 is held in place by adhesive 15 and makes electrical contact with electrically conductive film 22. Insulative portion 28 of lead wire 14 is contained under the edge of protective web 12 in order to have a completely insulated biomedical electrode 10E system.

Figure 8:
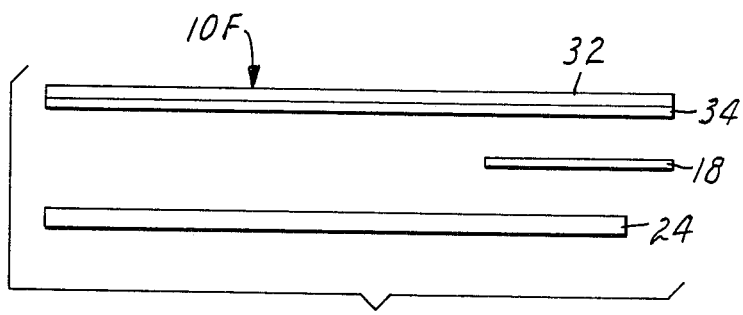
FIG. 8 is a side view of an alternative embodiment of the biomedical electrode of the present invention.

The biomedical electrode 10F illustrated in FIG. 8 is similar to the biomedical electrode 10D illustrated in FIG. 6. Biomedical electrode 10F has a top layer consisting of a protective electrically insulative web 32 which in a preferred embodiment is an electrically insulative plastic sheet. The bottom side of protective web 32 is coated with an electrically conductive metallic coating 34 which in a preferred embodiment is aluminum which has been vapor coated onto the protective web 32 preferably in thicknesses of from 700 to 1200 angstroms. A release liner 18 with the release agent facing downward is positioned adjacent to the metallic coating 34 and covers a portion of the surface area of the biomedical electrode 10F. An electrically conductive adhesive 24 of the same type as described in FIG. 2 is then located below release liner 18 and is directly attached to release liner 18 or metallic coating 34. In use, biomedical electrode 10F may be applied to the body by electrically conductive adhesive 24. Release liner 18 may be removed and an electrical lead wire (not shown) may be inserted in place of the release liner 18. Once the electrical lead wire is placed, the protective web 32 may be resecured over the top of the electrical lead wire. Electrically conductive adhesive 24 holds both the electrical lead wire and protective web 32 in place. Metallic coating 34 over the lower surface of protective web 32 helps distribute the electrical current supplied from or to the electrical lead wire over the entire surface area of biomedical electrode 10F. In a preferred embodiment, protective web 32 with metallic coating 34 and release liner 18 extend beyond one edge of electrically conductive adhesive 24 so that they may be easily grasped to facilitate easy removal of release liner 18 when required.

Although biomedical electrode 10 has been illustrated as being in generally rectangular shaped it is to recognized and understood that any suitable shape, size or configuration of biomedical electrode 10 may be utilized to fit or suit the particular environment or body part to which it is adapted to be applied.

Thus, it can be seen that there has been shown and described a novel, flat, conformable, biomedical electrode. It is to be recognized and understood, however, that various changes, modifications and substitutions in the form and of the details of the present invention can be made by those skilled in the art without departing from the scope of the invention as defined by the following claims.

What is claimed is:

1. A biomedical electrode adapted to be applied to a body, comprising:
   a protective, electrically insulative web;
   a first layer of adhesive adjacent one side of said protective, electrically insulative web, said one side adapted to be oriented toward said body;
   a release liner adjacent said first layer of adhesive and opposite said protective, electrically insulative web, said release liner having a release agent facing said first layer of adhesive, said release liner covering only a portion of the surface area of said protective, electrically insulative web;
   an electrically conductive film positioned adjacent said first layer of adhesive and said release liner;
   a second layer of adhesive which is electrically conductive and positioned adjacent said electrically conductive film opposite said first layer of adhesive and adapted to be applied to said body; and
   an electrical lead wire having a distal uninsulated portion and a proximate insulated portion, said distal end uninsulated portion of said electrical lead wire being inserted between said first layer of adhesive and said electrically conductive film and at least part of said proximate insulated portion of said electrical lead wire extending under an edge of said protective, electrically insulative web.

2. A biomedical electrode as in claim 1 wherein said electrically conductive film has a metallic coating.

3. A biomedical electrode as in claim 2 wherein said metallic coating faces said first layer of adhesive.

4. A biomedical electrode as in claim 1 wherein said second layer of adhesive contains silver particles.

5. A biomedical electrode as in claim 1 wherein said protective, electrically insulative web is perforated.

6. A biomedical electrode as in claim 1 wherein said protective, electrically insulative web is embossed.

* * * * *